(12) United States Patent
Smits

(10) Patent No.: US 8,532,789 B2
(45) Date of Patent: Sep. 10, 2013

(54) SUBCUTANEOUS LEAD FIXATION MECHANISMS

(75) Inventor: Karel Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 549 days.

(21) Appl. No.: 11/364,308

(22) Filed: Feb. 28, 2006

(65) Prior Publication Data

US 2007/0203553 A1 Aug. 30, 2007

(51) Int. Cl.
*A61N 1/00* (2006.01)

(52) U.S. Cl.
USPC ........... 607/122; 607/119; 607/128; 607/129; 607/130

(58) Field of Classification Search
USPC .................. 607/122, 119, 175, 128, 129, 130
See application file for complete search history.

(56) References Cited

U.S. PATENT DOCUMENTS

| | | | |
|---|---|---|---|
| 4,180,078 A | 12/1979 | Anderson | |
| 4,374,382 A | 2/1983 | Markowitz | |
| 4,548,209 A | 10/1985 | Wielders et al. | |
| 4,553,961 A * | 11/1985 | Pohndorf et al. | 604/175 |
| 4,556,063 A | 12/1985 | Thompson et al. | |
| 4,582,056 A * | 4/1986 | McCorkle, Jr. | 606/1 |
| 5,127,404 A | 7/1992 | Wyborny et al. | |
| 5,152,298 A | 10/1992 | Kreyenhagen et al. | |
| 5,163,427 A | 11/1992 | Keimel | |
| 5,188,105 A | 2/1993 | Keimel | |
| 5,193,535 A | 3/1993 | Bardy et al. | |
| 5,242,430 A * | 9/1993 | Arenas et al. | 16/110.1 |
| 5,354,316 A | 10/1994 | Keimel | |
| 5,470,345 A | 11/1995 | Hassler et al. | |
| 5,545,186 A | 8/1996 | Olson et al. | |
| 5,628,780 A * | 5/1997 | Helland et al. | 607/126 |
| 5,683,432 A | 11/1997 | Goedeke et al. | |
| 5,855,593 A | 1/1999 | Olson et al. | |
| 5,876,429 A * | 3/1999 | Schroeppel | 607/115 |
| 6,213,988 B1 * | 4/2001 | McIvor et al. | 604/264 |
| 7,184,341 B2 * | 2/2007 | Yuan et al. | 365/203 |
| 7,184,841 B1 * | 2/2007 | Bodner et al. | 607/122 |
| 7,331,613 B2 * | 2/2008 | Schulte | 285/239 |
| 7,831,313 B2 * | 11/2010 | Lauro | 607/126 |
| 2004/0176782 A1 * | 9/2004 | Hanse et al. | 606/129 |
| 2004/0230274 A1 | 11/2004 | Heil et al. | |
| 2004/0236396 A1 | 11/2004 | Coe et al. | |
| 2005/0080471 A1 * | 4/2005 | Chitre et al. | 607/122 |
| 2005/0080472 A1 * | 4/2005 | Atkinson et al. | 607/126 |
| 2006/0009830 A1 * | 1/2006 | Atkinson et al. | 607/126 |
| 2006/0036307 A1 * | 2/2006 | Zarembo et al. | 607/122 |

FOREIGN PATENT DOCUMENTS

EP 0159540 A1 10/1985

* cited by examiner

*Primary Examiner* — Niketa Patel
*Assistant Examiner* — Mallika D Fairchild
(74) *Attorney, Agent, or Firm* — Carol F. Barry

(57) ABSTRACT

A medical device that includes a lead having a lead body extending from a proximal end to a distal end, and a housing having a connector block for receiving the proximal end of the lead body. A fixation mechanism is positioned proximal to an electrode coil located at the distal end of the lead body, and includes a locking sleeve and a mating portion positioned along the lead body proximal to the electrode. The fixation mechanism is capable of being advance from a first state corresponding to a first inner diameter of the locking sleeve and a second state corresponding to a second inner diameter of the locking sleeve greater than the first inner diameter to fixed position the electrode at a target site.

19 Claims, 7 Drawing Sheets

SUBCUTANEOUS LEAD FIXATION MECHANISMS

FIELD OF THE INVENTION

The present invention generally relates to an implantable subcutaneous lead for use with an implantable medical device, and more particularly, to a lead that includes deployable fixation means for positively fixating the lead at an implantation site.

BACKGROUND OF THE INVENTION

Many types of implantable medical devices (IMDs) have been clinically implanted over the last twenty years that deliver relatively high-energy cardioversion and/or defibrillation shocks to a patient's heart when a malignant tachyarrhythmia, e.g., atrial or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the EGM.

Current implantable cardioverter/defibrillators (ICDs) or implantable pacemaker/cardioverter/defibrillators (PCDs) include programmable parameters such as multiple arrhythmia detection criteria/levels, multiple therapy prescriptions (e.g., stimulation at pacing levels (atrial/ventricular/dual chamber atrial & ventricular for bradycardia, bi-atrial and/or bi-ventricular for heart failure patients and arrhythmia overdrive or entrainment stimulation) and high level stimulation via cardioversion and/or defibrillation), extensive diagnostic capabilities and high speed telemetry systems. These ICDs or PCDs are typically implanted into patients who have experienced a significant cardiac event.

Attempts at identifying those patients who are asymptomatic by conventional measures but are nevertheless at risk of a future sudden death episode are being undertaken. Current studies of patient populations, e.g., the MADIT II and SCD-HeFT studies, are establishing that there are large numbers of patients in any given population that are susceptible to sudden cardiac death, and that they can be identified with some degree of certainty. One option proposed for this patient population is to implant a prophylactic subcutaneous implantable cardioverter/defibrillator (SubQ ICD) to deliver therapy in the event of a cardiac episode, such as sudden cardiac arrest, in order to reduce the risk of death resulting from the episode, and who will then have a full-featured ICD with transvenous leads implanted.

Current implanted subcutaneous coil leads are complicated and time consuming to implant and may dislodge or pull back acutely. Further, fibrosis and tissue build-up make it impossible to remove intracardial leads after a few month of implant.

Therefore, for these and other reasons, a need exists for an improved method and apparatus for a subcutaneously implanted lead that is easy to implant and stays fixed in the proper location acutely and chronically, or until it becomes desirable to remove the lead for repositioning or remove the lead permanently.

BRIEF DESCRIPTION OF THE DRAWINGS

Embodiments of the present invention will be appreciated as the same becomes better understood by reference to the following detailed description of the specific embodiments of the invention when considered in connection with the accompanying drawings, in which like numbered reference numbers designate like parts throughout the figures thereof, and wherein.

DETAILED DESCRIPTION OF THE INVENTION

Figure 1:
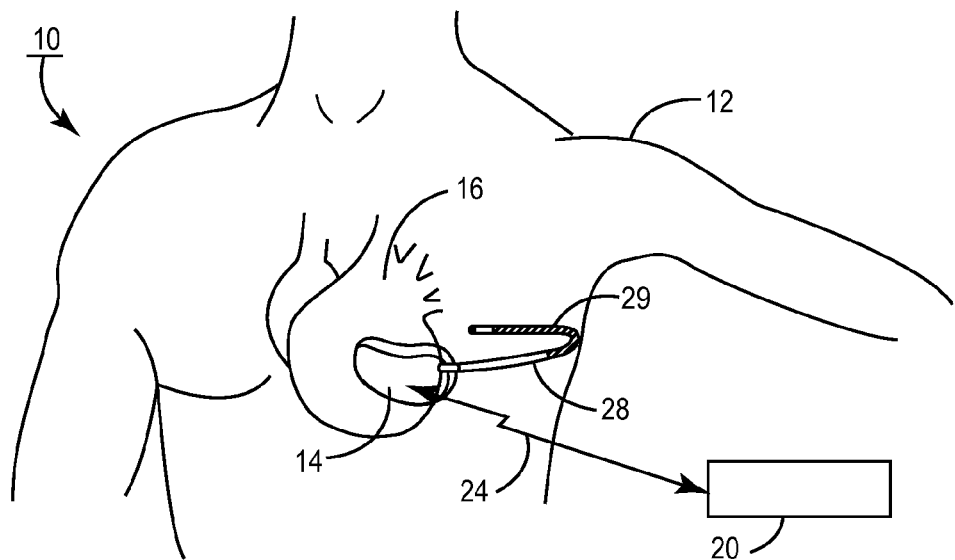
FIG. 1 is a schematic diagram of a subcutaneous medical device implanted in a patient according to an embodiment of the present invention.

FIG. 1 is a schematic diagram of a subcutaneous medical device implanted in a patient according to an embodiment of the present invention. As illustrated in FIG. 1, a subcutaneous medical device includes a hermetically sealed housing 14 that is subcutaneously implanted outside a patient's 12 ribcage anterior to the cardiac notch and a subcutaneous sensing and cardioversion/defibrillation therapy delivery lead 28 extending from the housing 14 to be positioned in relation to the heart 16. The cardiac notch is the lateral deflection of the anterior border/boundary of the left lung, which accommodates the space taken up by the heart. Lead 28 is tunneled subcutaneously from the median implant pocket of housing 14 laterally and posteriorly to the patient's back to a location opposite the heart such that the heart 16 is disposed between the housing 14 and a distal electrode coil 29 of subcutaneous lead 28.

Further referring to FIG. 1, a programmer 20 may be positioned in telemetric communication with circuitry contained within housing 14 via an RF communication link 24, such as Bluetooth, WiFi, MICS, for example, or as described in U.S. Pat. No. 5,683,432 "Adaptive Performance-Optimizing Communication System for Communicating with an Implantable Medical Device" to Goedeke, et al and incorporated herein by reference in its entirety.

Figure 2A:
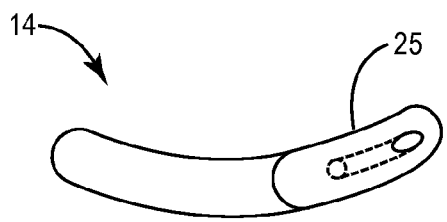
FIG. 2A is a top view of a device housing according to an embodiment of the present invention.
Figure 2B:
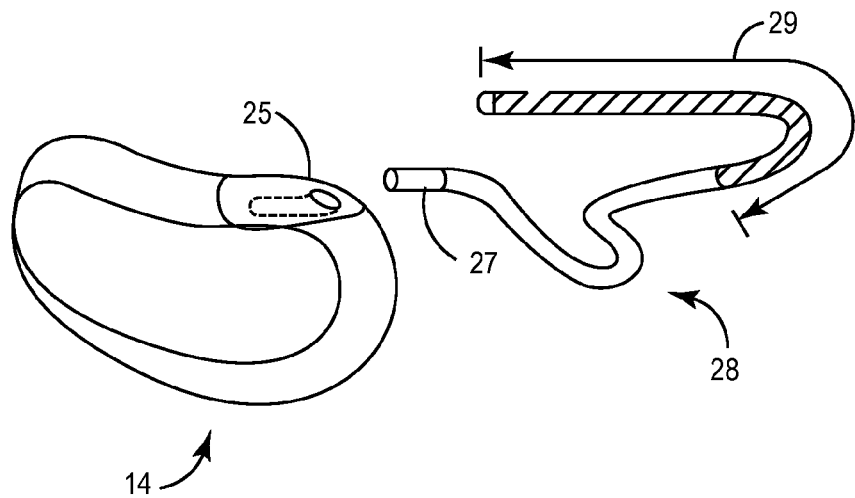
FIG. 2B is a schematic diagram of a device housing and a lead according to an embodiment of the present invention.

FIG. 2A is a top view of a device housing according to an embodiment of the present invention. FIG. 2B is a schematic diagram of a device housing and a lead according to an embodiment of the present invention. As illustrated in FIGS. 2A and 2B, housing 14 may have a concave, substantially kidney shaped, for example, with a connector block 25 for receiving a proximal connector pin 27 of subcutaneous sensing and cardioversion/defibrillation therapy delivery lead 28 and electrically connecting the lead 28 to the circuitry within housing 14. Housing 14 may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronic circuitry located in housing 14 of subcutaneous cardioverter-defibrillator (described later in relation to FIGS. 3-4) may be incorporated on a polyamide flex circuit, printed circuit board (PCB) or ceramic substrate with integrated circuits packaged in leadless chip carriers and/or chip scale packaging (CSP). Housing 14 is formed having a concave construction enabling un-obtrusive subcutaneous implant by the concave structure of the canister following the natural curve of the patient's median ribcage at the cardiac notch. This structure also minimizes patient discomfort when seated, bending over and/or during normal torso movement.

The electronic circuitry in housing 14 (as described above in relation to FIGS. 1-2) includes circuitry for performing any desired known sensing and or/therapy delivery function(s), such as detection a tachyarrhythmia from the sensed ECG and delivering cardioversion/defibrillation therapy, as well as post-shock pacing as needed while the heart recovers. A simplified block diagram of such circuitry adapted to function employing the first and second and, optionally, the third cardioversion-defibrillation electrodes as well as the ECG sensing and pacing electrodes described above is set forth in FIG. 3. It will be understood that the simplified block diagram does not show all of the conventional components and circuitry of such ICDs including digital clocks and clock lines, low voltage power supply and supply lines for powering the circuits and providing pacing pulses or telemetry circuits for telemetry transmissions between housing of the SubQ ICD and an external programmer (20 of FIG. 1).

Figure 3:
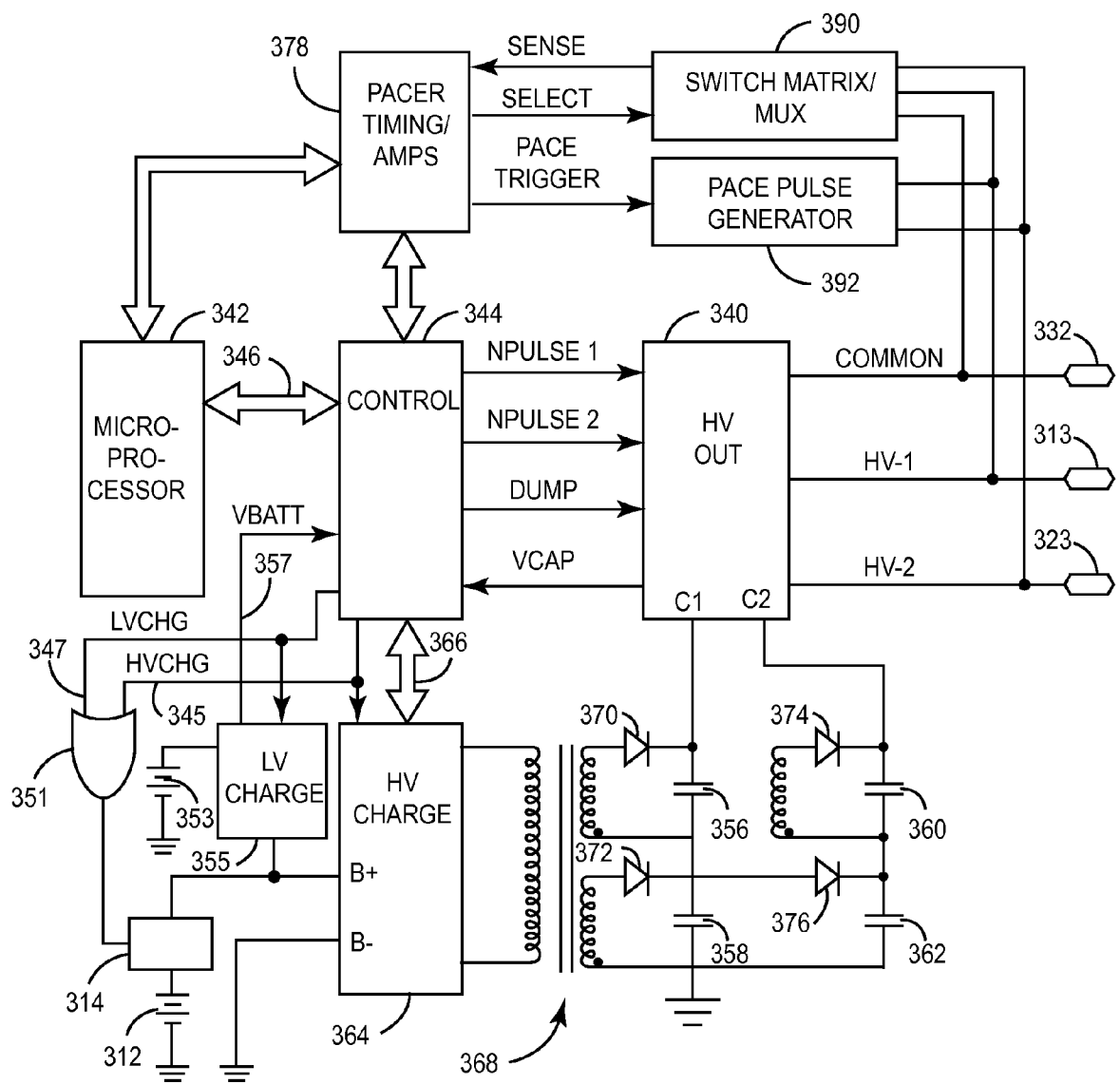
FIG. 3 is a schematic diagram of electronic circuitry included in a medical device according to an embodiment of the present invention.

FIG. 3 is a schematic diagram of electronic circuitry included in a medical device according to an embodiment of the present invention. As illustrated in FIG. 3, a low voltage battery 353 is coupled to a power supply (not shown) that supplies power to the ICD circuitry and the pacing output capacitors to supply pacing energy in a manner well known in the art. The low voltage battery may include one or two conventional $LiCF_x$, $LiMnO_2$ or $LiI_2$ cells, for example, and a high voltage battery 312 may include one or two conventional $LiSVO$ or $LiMnO_2$ cell.

In FIG. 3, ICD functions are controlled by means of stored software, firmware and hardware that cooperatively monitor the EGM, determine when a cardioversion-defibrillation shock or pacing is necessary, and deliver prescribed cardioversion-defibrillation and pacing therapies. The schematic diagram of FIG. 3 incorporates circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, for example, both incorporated herein by reference in their entireties, for selectively delivering single phase, simultaneous biphasic and sequential biphasic cardioversion-defibrillation shocks typically employing an ICD IPG housing electrode coupled to the COMMON output 312 of high voltage output circuit 340 and one or two cardioversion-defibrillation electrodes disposed posterially and subcutaneously and coupled to the HVI and HV-2 outputs (313 and 323, respectively) of the high voltage output circuit 340. The circuitry of the SubQ ICD 14 of the present invention can be made simpler by adoption of one such cardioversion-defibrillation shock waveform for delivery simply between the first and second cardioversion-defibrillation electrodes 313 and 323 coupled to the HV-I and HV-2 outputs respectively. Alternatively, the third cardioversion-defibrillation electrode 332 can be coupled to the COMMON output as depicted in FIG. 3 and the first and second cardioversion-defibrillation electrodes 313 and 323 can be electrically connected in to the HV-1 and the HV-2 outputs, respectively, as depicted in FIG. 3.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the waveform used. The SubQ ICD of the present invention uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation shocks are only delivered when a malignant tachyarrhythmia, e.g., ventricular fibrillation is detected through processing of the far field cardiac ECG employing one of the available detection algorithms known in the ICD art.

In FIG. 3, pacer timing/sense amplifier circuit 378 processes the far field ECG SENSE signal that is developed across a particular ECG sense vector defined by a selected pair of the electrodes 332, 313 and, optionally, electrode 323 if present as noted above. The selection of the sensing electrode pair is made through the switch matrix/MUX 390 in a manner to provide the most reliable sensing of the EGM signal of interest, which would be the R wave for patients who are believed to be at risk of ventricular fibrillation leading to sudden death. The far field ECG signals are passed through the switch matrix/MUX 390 to the input of a sense amplifier in the pacer timing/sense amplifier circuit 378. Bradycardia is typically determined by an escape interval timer within the pacer timing circuit 378 or the timing and control circuit 344, and pacing pulses that develop a PACE TRIGGER signal applied to the pacing pulse generator 392 when the interval between successive R-waves exceeds the escape interval. Bradycardia pacing is often temporarily provided to maintain cardiac output after delivery of a cardioversion-defibrillation shock that may cause the heart to slowly beat as it recovers function.

Detection of a malignant tachyarrhythmia is determined in the timing and control circuit 344 as a function of the intervals between R-wave sense event signals that are output from the pacer timing/sense amplifier circuit 378 to the timing and control circuit 344.

Certain steps in the performance of the detection algorithm criteria are cooperatively performed in a microcomputer 342, including microprocessor, RAM and ROM, associated circuitry, and stored detection criteria that may be programmed into RAM via a telemetry interface (not shown) conventional in the art. Data and commands are exchanged between microcomputer 342 and timing and control circuit 344, pacer timing/amplifier circuit 378, and high voltage output circuit 340 via a bidirectional data/control bus 346. The pacer timing/amplifier circuit 378 and the timing and control circuit 344 are clocked at a slow clock rate. The microcomputer 342 is normally asleep, but is awakened and operated by a fast clock by interrupts developed by each it-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 378. The algorithms and functions of the microcomputer 342 and timer and control circuit 344 employed and performed in detection of tachyarrhythmias are set forth, for example, in commonly assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al, U.S. Pat. No. 5,855,593 "Prioritized Rule Based Method and Apparatus for Diagnosis and Treatment of Arrhythmias" to Olson, et al and U.S. Pat. No. 5,193,535 "Method and Apparatus for Discrimination of Ventricular Tachycardia from Ventricular Fibrillation and Treatment Thereof" to Bardy, et al, (all incorporated herein by reference in their entireties). Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '316, '186, '593 and '593 patents.

The detection algorithms are highly sensitive and specific for the presence or absence of life threatening ventricular arrhythmias, e.g., ventricular tachycardia (V-TACH) and ventricular fibrillation (V-FIB). Another optional aspect of the present invention is that the operational circuitry can detect the presence of atrial fibrillation (A FIB) as described in Olson, W. et al. "Onset And Stability For Ventricular Tachyarrhythmia Detection in an Implantable Cardioverter and Defibrillator," Computers in Cardiology (1986) pp. 167-170. Detection can be provided via R-R Cycle length instability detection algorithms. Once A-FIB has been detected, the operational circuitry will then provide QRS synchronized atrial cardioversion/defibrillation using the same shock energy and wave shapes used for ventricular cardioversion/defibrillation.

Operating modes and parameters of the detection algorithm are programmable and the algorithm is focused on the detection of V-FIB and high rate V-TACH (>240 bpm).

Although the ICD of the present invention may rarely be used for an actual sudden death event, the simplicity of design and implementation allows it to be employed in large populations of patients at modest risk with modest cost by medical personnel other than electrophysiologists. Consequently, the ICD of the present invention includes the automatic detection and therapy of the most malignant rhythm disorders. As part of the detection algorithm's applicability to children, the upper rate range is programmable upward for use in children, known to have rapid supraventricular tachycardias and more rapid V-FIB.

When a malignant tachycardia is detected, high voltage capacitors 356, 358, 360, and 362 are charged to a pre-programmed voltage level by a high-voltage charging circuit 364. It is generally considered inefficient to maintain a constant charge on the high voltage output capacitors 356, 358, 360, 362. Instead, charging is initiated when control circuit 344 issues a high voltage charge command HVCHG delivered on line 345 to high voltage charge circuit 364 and charging is controlled by means of bidirectional control/data bus 366 and a feedback signal VCAP from the HV output circuit 340. High voltage output capacitors 356, 358, 360 and 362 may be of film, aluminum electrolytic or wet tantalum construction.

The negative terminal of high voltage battery 312 is directly coupled to system ground. Switch circuit 314 is normally open so that the positive terminal of high voltage battery 312 is disconnected from the positive power input of the high voltage charge circuit 364. The high voltage charge command HVCHG is also conducted via conductor 349 to the control input of switch circuit 314, and switch circuit 314 closes in response to connect positive high voltage battery voltage EXT B+ to the positive power input of high voltage charge circuit 364. Switch circuit 314 may be, for example, a field effect transistor (FET) with its source-to-drain path interrupting the EXT B+conductor 318 and its gate receiving the HVCHG signal on conductor 345. High voltage charge circuit 364 is thereby rendered ready to begin charging the high voltage output capacitors 356, 358, 360, and 362 with charging current from high voltage battery 312.

High voltage output capacitors 356, 358, 360, and 362 may be charged to very high voltages, e.g., 700-3150V, to be discharged through the body and heart between the selected electrode pairs among first, second, and, optionally, third subcutaneous cardioversion-defibrillation electrodes 313, 323, and 332. The details of the voltage charging circuitry are also not deemed to be critical with regard to practicing the present invention; one high voltage charging circuit believed to be suitable for the purposes of the present invention is disclosed. High voltage capacitors 356, 358, 360, and 362 are charged by high voltage charge circuit 364 and a high frequency, high-voltage transformer 368 as described in detail in commonly assigned U.S. Pat. No. 4,548,209 "Energy Converter for Implantable Cardioverter" to Wielders, et al. Proper charging polarities are maintained by diodes 370, 372, 374 and 376 interconnecting the output windings of high-voltage transformer 368 and the capacitors 356, 358, 360, and 362. As noted above, the state of capacitor charge is monitored by circuitry within the high voltage output circuit 340 that provides a VCAP, feedback signal indicative of the voltage to the timing and control circuit 344. Timing and control circuit 344 terminates the high voltage charge command HVCHG when the VCAP signal matches the programmed capacitor output voltage, i.e., the cardioversion-defibrillation peak shock voltage.

Timing and control circuit 344 then develops first and second control signals NPULSE 1 and NPULSE 2, respectively, that are applied to the high voltage output circuit 340 for triggering the delivery of cardioverting or defibrillating shocks. In particular, the NPULSE 1 signal triggers discharge of the first capacitor bank, comprising capacitors 356 and 358. The NPULSE 2 signal triggers discharge of the first capacitor bank and a second capacitor bank, comprising capacitors 360 and 362. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 344 serves to control operation of the high voltage output stage 340, which delivers high energy cardioversion-defibrillation shocks between a selected pair or pairs of the first, second, and, optionally, the third cardioversion-defibrillation electrodes 313, 323, and 332 coupled to the HV-1, HV-2 and optionally to the COMMON output as shown in FIG. 3.

Thus, ICD 10 monitors the patient's cardiac status and initiates the delivery of a cardioversion-defibrillation shock through a selected pair or pairs of the first, second and third cardioversion-defibrillation electrodes 313, 323 and 332 in response to detection of a tachyarrhythmia requiring cardioversion-defibrillation. The high HVCHG signal causes the high voltage battery 312 to be connected through the switch circuit 314 with the high voltage charge circuit 364 and the charging of output capacitors 356, 358, 360, and 362 to commence. Charging continues until the programmed charge voltage is reflected by the VCAP signal, at which point control and timing circuit 344 sets the HVCHG signal low terminating charging and opening switch circuit 314. Typically, the charging cycle takes only fifteen to twenty seconds, and occurs very infrequently. The ICD 10 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the ICD 10 on a prophylactic basis would be instructed to report each such episode to the attending physician for further evaluation of the patient's condition and assessment for the need for implantation of a more sophisticated and long-lived ICD.

Housing 14 may include telemetry circuit (not shown in FIG. 3), so that it is capable of being programmed by means of external programmer 20 via a 2-way telemetry link 24 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bidirectional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following commonly assigned U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device", each hereby incorporated by reference herein in their respective entireties.

Figure 4:
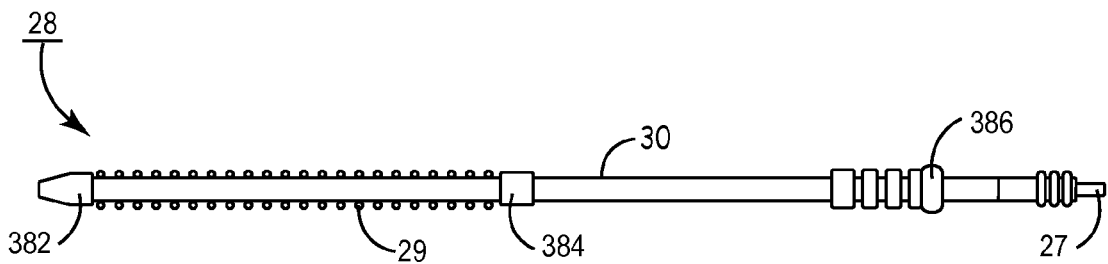
FIG. 4 is a schematic diagram of a subcutaneous lead of a medical device according to an embodiment of the present invention.

FIG. 4 is a schematic diagram of a subcutaneous lead of a medical device according to an embodiment of the present invention. As illustrated in FIG. 4, the lead 28 includes a lead body 30 that extends from lead connector pin 27 at the proximal end of the lead 28 to a distal tip 382 positioned at the distal end of the lead 28. A proximal suture sleeve 386 is positioned distally from the connector pin 27 and a distal electrode coil 29 is positioned at the distal end of the lead and extends proximally along the lead body 30 from the distal end of the lead 28. Lead 28 of the present invention includes a proximal fixation mechanism 384, and in such an embodiment the electrode coil 29 may extend from the distal tip 382 to the proximal fixation mechanism 384 so that the proximal fixation mechanism 384 is located just proximal to the electrode coil 29. The distal tip 382 may be formed of a flexible or pliant material such as polymeric material, silicone rubber or polyurethane. The electrode coil 29 may be formed of platinum, titanium or platinum iridium alloy. The lead body 28 may be formed of any flexible insulating material such as silicone rubber or polyurethane. The proximal lead pin 27 is electrically coupled to an insulated cable extending the length of the lead body 28 and electrically coupled to the electrode coil 29.

Figure 5A:
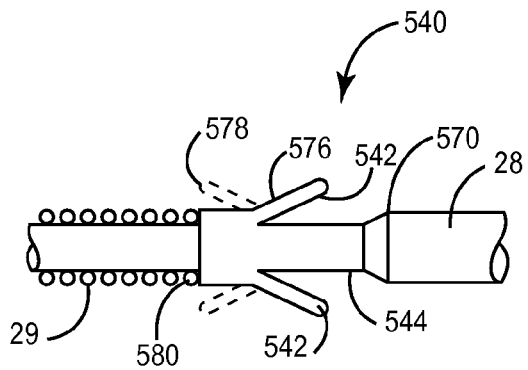
FIG. 5A is a side view of fixation apparatus positioned at a proximal end of a coil electrode of a subcutaneous lead of a medical device according to an embodiment of the present invention.
Figure 5B:
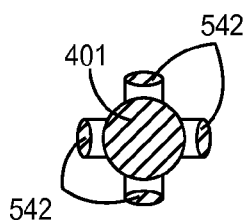
FIG. 5B is an end view of the distal end of the subcutaneous lead of FIG. 5A.

FIG. 5A is a side view of fixation apparatus positioned at a proximal end of a coil electrode of a subcutaneous lead of a medical device according to an embodiment of the present invention. FIG. 5B is an end view of the distal end of the subcutaneous lead of FIG. 5A. As illustrated in FIGS. 5A and 5B, the proximal fixation apparatus 540 is positioned proximal from the coil electrode 29 of the lead 28, and includes 4 proximal tines 542 formed of flexible or pliant material such as polymeric materials for example, as silicone rubber or polyurethane. The fixation apparatus 540 extends from a proximal end 570 to a distal end 580, with the distal end 580 having a diameter greater than the proximal end 570 corresponding to the thickness of one of the tines 542 so that the tines 542 fold back and engage against a body portion 544 of the fixation apparatus 540 when the lead 28 is positioned within a tunneling sheath. Upon delivery to the proper location, the sheath is retracted from the lead 28 allowing the tines 542 to return to their extended position 576 whereby they push against the subcutaneous tunneled wall improving both acute and chronic fixation. For chronic lead removal, the tines 542 will reverse their orientation to be in a retraction position 578 extending in a direction opposite when in the extended position 576, toward the distal electrode coil 29, during lead retraction thus enabling ease of removal. This embodiment has an advantage in that the thickest portion of the lead is not located at the distal end of the lead near the spinal column but more on the patient's lateral side thus promoting less patient discomfort.

Figure 6A:
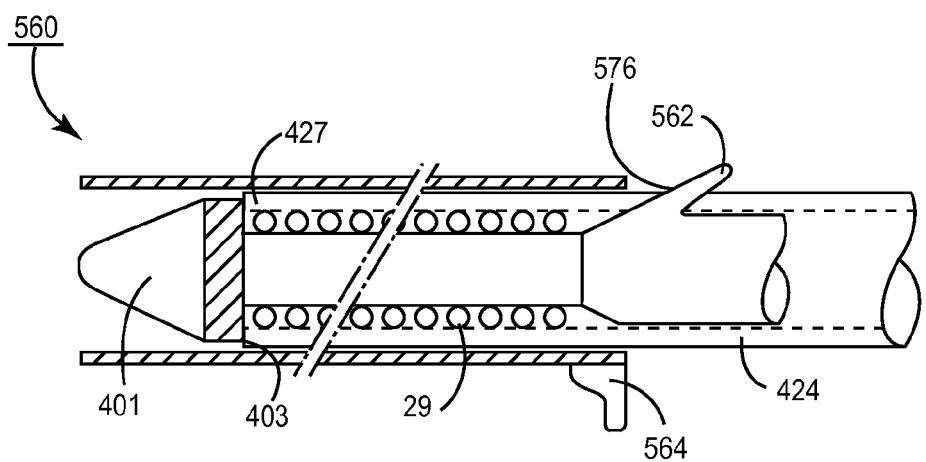
FIG. 6A is a side cut-away view of a subcutaneous lead of a medical device representing an embodiment of the present invention relating to a proximal fixation apparatus for anchoring subcutaneously tunneled lead.
Figure 6B:
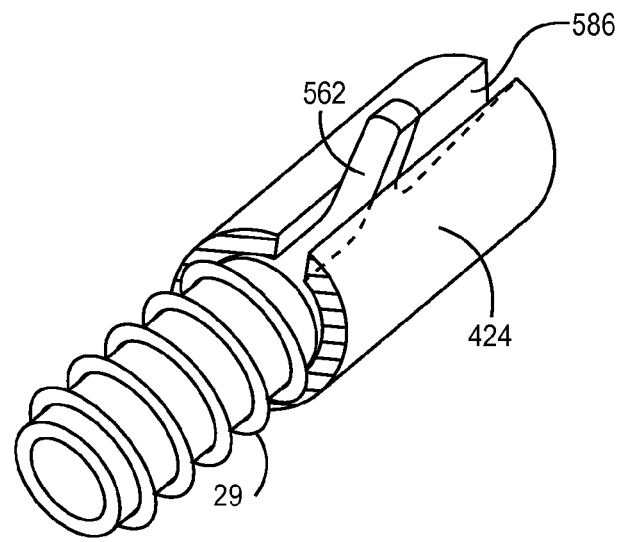
FIG. 6B is an oblique cut-away view of subcutaneous lead of FIG. 6A.
Figure 6C:
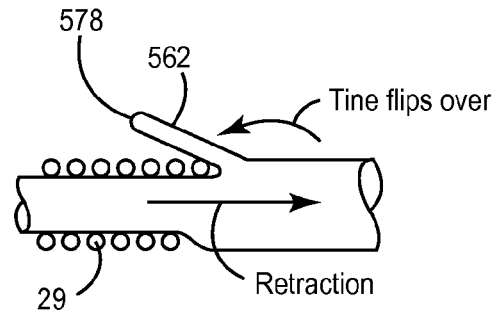
FIG. 6C is a side cut-away view of a subcutaneous lead of FIG. 6A showing further aspects of the invention.

FIG. 6A is a side cut-away view of a subcutaneous lead of a medical device representing an embodiment of the present invention relating to a proximal fixation apparatus for anchoring subcutaneously tunneled lead. FIG. 6B is an oblique cut-away view of subcutaneous lead of FIG. 6A. FIG. 6C is a side cut-away view of a subcutaneous lead of FIG. 6A showing further aspects of the invention. According to an embodiment of the present invention, a proximal fixation apparatus 560 includes a single proximal tine 562 formed of flexible or pliant material, for example, polymeric materials such as silicone rubber or polyurethane. The tine 562 is positioned within a longitudinal slot 586 formed along the length of a tunneling sheath 424 when the lead 28 is positioned the sheath 424.

The distal tip 401 of lead 28 includes a proximal end 403 that has a diameter greater than the diameter of the sheath 424 so that a distal end 427 of the sheath 424 engages against the proximal end 403 of the distal tip 401 as the sheath 424 is advanced through an introducer 564 (perspective view FIG. 6B). Upon delivery of the lead 28 to the proper location, the introducer 564 is removed from the sheath 424 by being slit using a slitting tool, for example, or other means known in the art. Because of the longitudinal slot 586 located along the sheath 424, the sheath does not have to be slit in order to remove the sheath 424 from the lead 28 subsequent to removing the introducer. Rather, the tine 562 advances through the slot 586 as the sheath 424 is retracted. In addition to reducing the effort required to remove the sheath 424 from the lead 28, by enabling the tine 562 to be positioned within the slot 564, the present invention reduces the length of the diameter required of the sheath 424 since the inner diameter of the sheath 424 does not have to accommodate the tine 562, thereby reducing the required size of the introducer 564. Retraction of the sheath 424 allows the tine 562 to push against the tunneled subcutaneous wall improving both acute and chronic fixation. For chronic lead removal, the tine 562 will flip over during lead retraction from an extended position 576 away from coil electrode 29 to a retraction position 578 extending in a direction opposite to when the tine 562 is in the extended position 576, toward the distal electrode coil 29, for ease of removal (FIG. 6C).

Figure 7A:
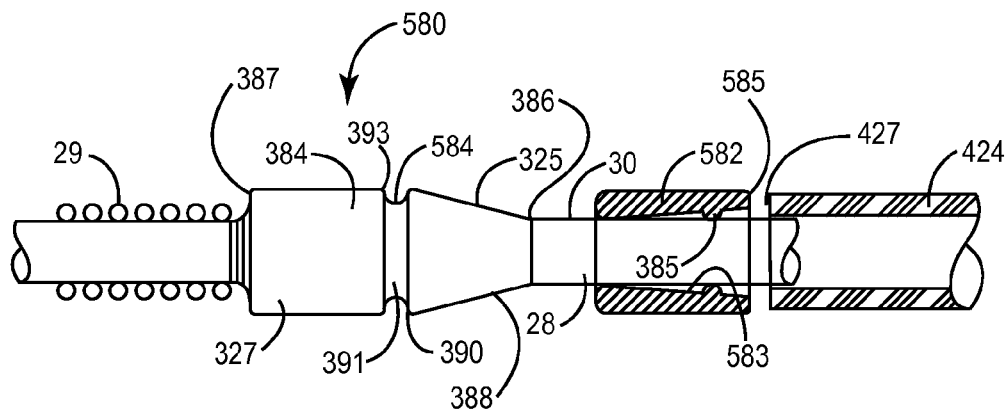
FIG. 7A is a side cut-away view of a subcutaneous lead of a medical device according to an embodiment of the present invention of a proximal fixation apparatus to anchor subcutaneously tunneled lead, according to an embodiment of the present invention.
Figure 7B:
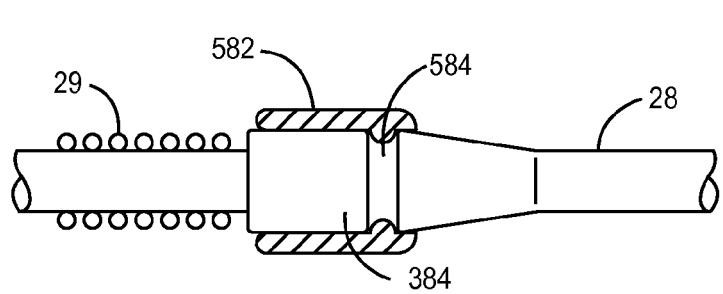
FIG. 7B is a side cut-away view of a subcutaneous lead of FIG. 7A.
Figure 7C:
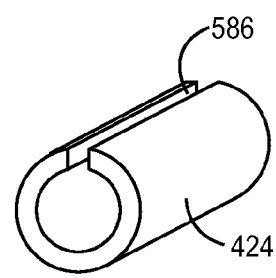
FIG. 7C is an oblique view of a further aspect of the subcutaneous lead of FIG. 7A.

FIG. 7A is a side cut-away view of a subcutaneous lead of a medical device according to an embodiment of the present invention of a proximal fixation apparatus to anchor subcutaneously tunneled lead, according to an embodiment of the present invention. FIG. 7B is a side cut-away view of a subcutaneous lead of FIG. 7A. FIG. 7C is an oblique view of a further aspect of the subcutaneous lead of FIG. 7A. The proximal fixation apparatus 580 of FIGS. 7A and 7B has a locking sleeve 582 formed of flexible or pliant material, for example, polymeric materials such as silicone rubber or polyurethane positioned over the lead body 30 of lead 28. The locking sleeve 582 includes a flange 385 extending circumferential outward from an inner surface 583 of the locking sleeve 582.

The lead includes a mating portion 384 positioned proximal to the coil electrode 29 that has a diameter greater than the diameter of the lead body 30. The mating portion 384 extends from a proximal end 386, having a diameter equal to the lead body 29, to a distal end 387, having a diameter greater than the lead body 30, with the distal end 387 positioned adjacent to the proximal end of the coil electrode 29. The mating portion 384 also includes a proximal section 325 and a distal section 327, with the proximal section 325 having a sloped portion 388 extending from the proximal end 386 to a sloped portion distal end 390, and the distal section 327 extending from a proximal end 393 to the distal end 387 of the mating portion 384. An intermediate section 391 is formed between the proximal section 325 and the distal section 327 and forms a channel 584 for receiving the flange 385 of the locking sleeve 582.

Upon delivery of the subcutaneous lead 28 to the proper location, the sheath 424 with a longitudinal slit 586 (FIG. 7C) is advanced forward so that distal end 427 of the sheath 424 engages against a proximal end 585 of the locking sleeve 582 and advances the locking sleeve 582 toward and over the mating portion 387 until the flange 385 is positioned within the channel 584 (FIG. 7B). The diameter of the compliant locking sleeve 582 is increased as the locking sleeve 582 is advanced over the sloped portion 388 to have an inner diameter approximately equal to the diameter of the distal section 327 of the mating portion 384, so that once the sheath 424 is retracted, the locking sleeve 582 pushes against the tunneled subcutaneous wall improving both acute and chronic fixation. For chronic lead removal, retraction force on the locking sleeve 582 will cause the locking sleeve 582 to unlock and allow the smaller diameter lead 28 to be retracted.

Figure 7D:
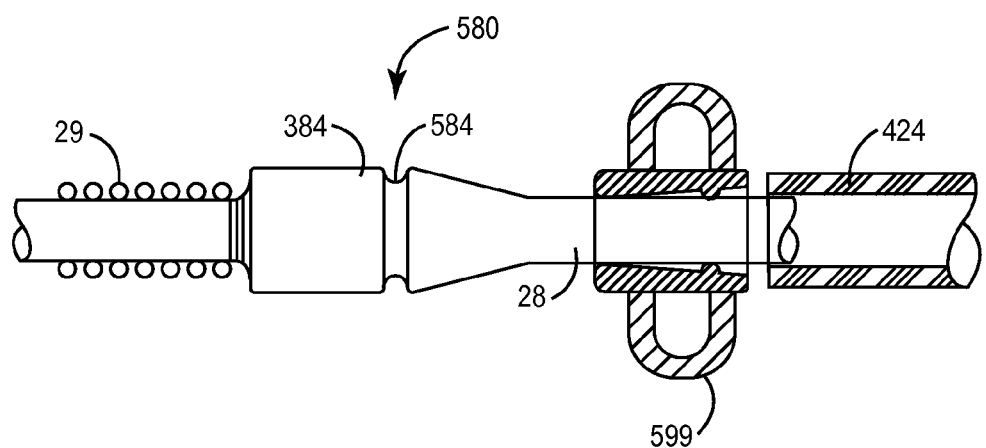
FIG. 7D a side cut-away view of a subcutaneous lead of a medical device according to an embodiment of the present invention.

FIG. 7D a side cut-away view of a subcutaneous lead of a medical device according to an embodiment of the present invention. As illustrated in FIG. 7D, the locking sleeve 582 may include one or more suture rings 599 to enable the device to be sutured at an incision site once the lead 28 positioned at the desire location within the patient.

Figure 8:
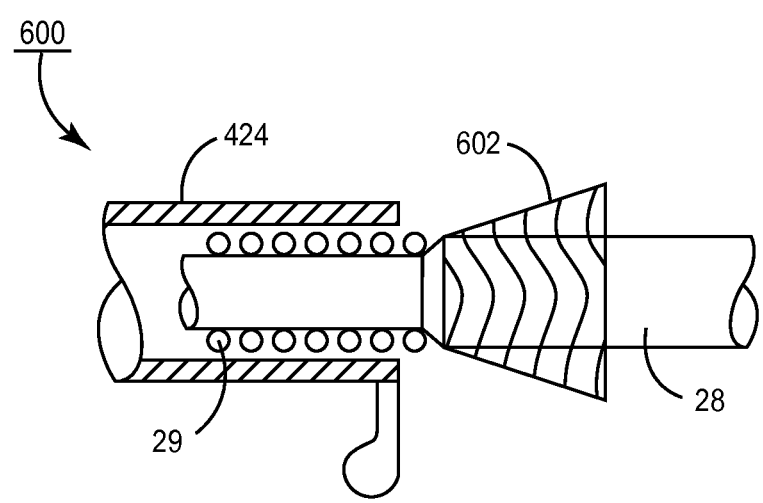
FIG. 8 is a side cut-away view of a subcutaneous lead of a medical device representing a proximal fixation apparatus to anchor subcutaneously tunneled lead, according to an embodiment of the present invention.

FIG. 8 is a side cut-away view of a subcutaneous lead of a medical device representing a proximal fixation apparatus to anchor subcutaneously tunneled lead, according to an embodiment of the present invention. As illustrated in FIG. 8, a proximal fixation apparatus 600 according to an embodiment of the present invention includes a self-expanding member 602 that is compressed when positioned within an introducer/sheath 424. Upon delivery to the proper location, the sheath 424 is retracted allowing the member 602 to expand, pushing against the subcutaneous tunneled wall and thereby clamping the lead in its location. The member 602 is formed of flexible or pliant material, for example, polymeric materials such as silicone rubber or polyurethane.

Figure 9:
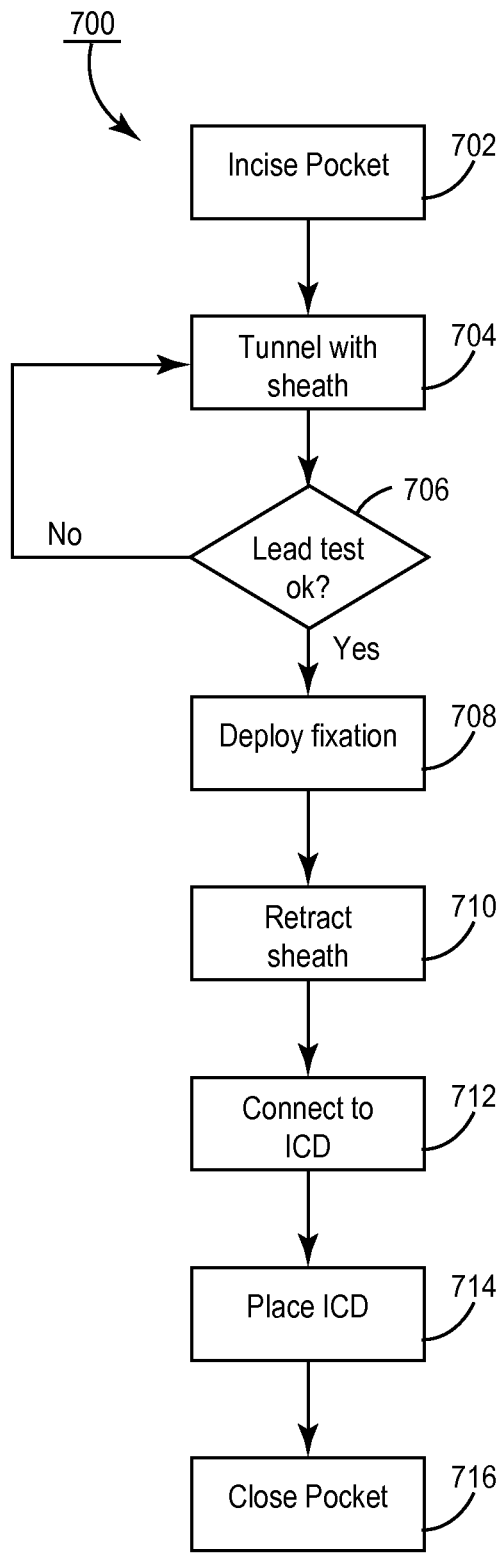
FIG. 9 is a flow chart of a method of fixedly positioning a subcutaneous lead according to an embodiment of the present invention.

FIG. 9 is a flow chart of a method of fixedly positioning a subcutaneous lead according to an embodiment of the present invention. As illustrated in FIG. 9 at step 702, the physician incises the subcutaneous implant site pocket for the housing 14 medially anterior to the cardiac notch. At step 704, the physician tunnels with an introducer/tunneling tool subcutaneously from the median implant pocket of housing 14 laterally and posteriorly to the patient's back to a location opposite the heart such that the heart 16 is disposed between the housing 14 and the distal end of subcutaneous lead 28. Tunneling is typically just above muscle subcutaneously crossing over ribs to prevent inadvertent entrance into the thoracic cavity/lungs. The implant location of device 14 and lead 28 is typically between the $3^{rd}$ and $8^{th}$ ribs. At step 706, the location of the electrode 29 of lead 28 is tested for proper sensing and positioning. If the test results are adequate, the process continues to step 708. If however, at step 706 the test results are inadequate, the process returns to step 704 to further continue tunneling and repositioning the electrode 29. At step 708, the physician deploys the fixation apparatus of the present invention. For example, with the lead designs as described above in relation to FIGS. 5, 6 and 8, the sheath is retracted to deploy the inventive fixation apparatus. In the lead design as described above in relation to FIG. 7, the sheath is advanced through an introducer or tunneling tool to place the fixation sleeve in its locked position and is subsequently retracted.

Continuing with flow diagram 700, at step 710, the housing 14 is connected to the subcutaneous lead 28 proximal pin 27. At step 712 the SubQ ICD is placed in the implant pocket and the incision closed at step 714. Additional testing and programming via external programmer 20 may subsequently then be performed as is well know in the art.

It will be apparent from the foregoing that while particular embodiments of the invention have been illustrated and described, various modifications can be made without departing from the spirit and scope of the invention. Accordingly, it is not intended that the invention be limited, except as by the appended claims.

What is claimed is:

1. A medical device system including an electrode configured to be subcutaneously placed at a target site in a patient using a lead that is adapted to extend within a subcutaneous tunnel wall of a patient's body tissue formed outside a patient's vascular system, comprising:

the lead having a lead body extending from a proximal end to a distal end, the electrode configured to be positioned along the distal end of the lead; and a fixation mechanism configured to be positioned along the lead body proximal to the electrode, the fixation mechanism including a locking sleeve and a mating portion, the mating portion configured to be part of the lead body, the locking sleeve capable of being advanced distally along the lead body and over the mating portion, the locking sleeve having an inner surface facing the lead body and a flange extending from the inner surface of the locking sleeve toward the lead body, and the mating portion having a proximal section, a distal section and an intermediate section between the proximal section and the distal section, the intermediate section configured to form a channel for receiving the flange, wherein the proximal portion is sloped such that a diameter of the proximal section of the mating portion increases along a sloped surface from a proximal end of the proximal section to a distal end of the proximal section, wherein a diameter of the locking sleeve is increased as the locking sleeve is advanced over the proximal section of the mating portion, and wherein the flange has an inner diameter smaller than the inner diameter defined by the inner surface of the locking sleeve when the flange is located in the channel 2. The medical device system of claim 1, wherein a diameter of the distal section of the mating portion is greater than a diameter of the proximal section of the mating portion.

3. The medical device system of claim 1, further comprising an elongated member configured to receive the lead therein.

4. The medical device system of claim 3, wherein a distal end of the elongated member is configured to engage against a proximal end of the locking sleeve to advance the locking sleeve distally along the lead body and over the mating portion.

5. The medical device system of claim 1, wherein the flange is configured to fixedly engage within the channel when the locking sleeve is advanced over the mating portion.

6. The medical device system of claim 1, further comprising a suture ring configured to be positioned along the locking sleeve, wherein the suture ring comprises an opening.

7. A medical device system including an electrode configured to be subcutaneously placed at a target site in a patient using a lead that is adapted to extend within a subcutaneous tunnel wall of a patient's body tissue formed outside a patient's vascular system, comprising:

the lead having a lead body extending from a proximal end to a distal end, the electrode configured to be positioned along the distal end of the lead; and a fixation mechanism including a locking sleeve and a mating portion, the mating portion configured to be part of the lead body, the fixation mechanism configured to be positioned along the lead body proximal to the electrode, the mating portion having an outer diameter at a distal end section that is greater than a diameter of the lead body and having a sloped proximal section, wherein the outer diameter of the mating portion is progressively reduced when moving proximally along the sloped proximal section from a distal end of the proximal section to a proximal end of the proximal section, the locking sleeve configured to define a closed lumen with an inner diameter capable of being inserted over and encircling the lead body, the locking sleeve further capable of being advanced longitudinally along the lead body and over the mating portion, the locking sleeve being made of a compliant material wherein the inner diameter expands from a first state corresponding to a first inner diameter of the locking sleeve to a second state as the locking sleeve is advanced over the sloped proximal section of the mating portion and corresponding to a second inner diameter of the locking sleeve, the second inner diameter being greater than the first inner diameter, the second inner diameter of the locking sleeve being approximately equal to the outer diameter of the distal end section of the mating portion that is greater than the diameter of the lead body, the locking sleeve configured to have an inner surface facing the closed lumen and a flange extending from the inner surface of the locking sleeve toward the closed lumen, wherein the flange has an inner diameter smaller than the inner diameter defined by the inner surface of the locking sleeve when the flange is received in the channel.

8. The medical device system of claim 7, wherein the mating portion includes an intermediate section between the proximal section and the distal end section, wherein the channel is formed in the intermediate section.

9. The medical device system of claim 7, wherein a diameter of the distal end section of the mating portion is greater than a diameter of a proximal end of the proximal section of the mating portion.

10. The medical device system of claim 7, further comprising an elongated member configured to receive the lead therein.

11. The medical device system of claim 10, wherein a distal end of the elongated member is configured to engage against a proximal end of the locking sleeve to advance the locking sleeve distally along the lead body and over the mating portion.

12. The medical device system of claim 7, wherein the flange is configured to fixedly engage within the channel when the locking sleeve is advanced over the mating portion.

13. The medical device system of claim 7, further comprising a suture ring configured to be positioned along the locking sleeve, wherein the suture ring comprises an opening.

14. The medical device system of claim 7, wherein the first inner diameter is approximately equal to a diameter of the lead body.

15. A medical device system including an electrode configured to be subcutaneously placed at a target site in a patient using a lead that is adapted to extend within a subcutaneous tunnel wall of a patient's body tissue formed outside a patient's vascular system, comprising:

the lead having a lead body extending from a proximal end to a distal end, the electrode configured to be positioned along the distal end of the lead;

a fixation mechanism including a locking sleeve and a mating portion configured to be positioned along the lead body proximal to the electrode, the mating portion configured to be part of the lead body and comprising a sloped proximal section and a distal section, wherein a diameter of the distal section of the mating portion is greater than a diameter of a proximal end of the proximal section, wherein the diameter of the proximal section of the mating portion progressively increases from the proximal end of the proximal section to a distal end of the proximal section, the locking sleeve comprising an inner surface facing the lead body, the locking sleeve capable of being advanced distally along the lead body and over the proximal section of the mating portion from a first state along the lead body corresponding to a first inner diameter of the locking sleeve to a second state over the mating portion corresponding to a second inner diameter of the locking sleeve, the second inner diameter being greater than the first inner diameter;

a flange extending from the inner surface of the locking sleeve toward the lead body, the flange capable of being received within a channel formed by the mating portion of the fixation mechanism, wherein the flange has an inner diameter smaller than the inner diameter defined by the inner surface of the locking sleeve when the flange is located in the channel; and an elongated member configured to receive the lead therein, wherein a distal end of the elongated member engages against a proximal end of the locking sleeve to advance the locking sleeve distally along the lead body to the second state over the mating portion.

16. The medical device system of claim 15, wherein the mating portion includes an intermediate section between the proximal section and the distal section, wherein the channel is formed in the intermediate section.

17. The medical device system of claim 15, wherein the locking sleeve is capable of being advanced over the mating portion to have an inner diameter approximately equal to the diameter of the mating portion distal section, the increased diameter of the locking sleeve causing the locking sleeve to push against a tunneled subcutaneous wall to improve fixation of the lead.

18. A medical device system comprising:
a lead comprising:
  a lead body extending from a proximal end to a distal end,
  an electrode located proximate the distal end of the lead body, and
  a mating portion located between the proximal end and the electrode, wherein the mating portion comprises a proximal section, a distal section and an intermediate section between the proximal section and the distal section, wherein the intermediate section defines a channel, wherein a diameter of the distal section of the mating portion is greater than a diameter of the lead body, and wherein the proximal section of the mating portion is sloped such that a diameter of the proximal section of the mating portion increases from a proximal end of the proximal section to a distal end of the proximal section; and
a locking sleeve formed of compliant material, wherein the locking sleeve defines a closed lumen configured to receive the lead body such that that locking sleeve is capable of being advanced distally along the lead body and over the mating portion, wherein the locking sleeve comprises an inner surface facing the closed lumen and a flange extending from the inner surface of the locking sleeve toward the closed lumen, wherein the flange is configured to be received within the channel of the mating portion of the lead, wherein an inner diameter of the locking sleeve is increased when the locking sleeve is advanced over the proximal section of the mating portion, and wherein the flange has an inner diameter smaller than the inner diameter defined by the inner surface of the locking sleeve when the flange is located in the channel.

19. The medical device system of claim 18, wherein a diameter of the distal section of the mating portion is greater than a diameter of the proximal section of the mating portion.

* * * * *